United States Patent [19]

Stein et al.

[11] 4,200,654
[45] Apr. 29, 1980

[54] OVICIDES

[75] Inventors: Robert G. Stein, Kenosha, Wis.;
Terry L. Couch, Waukegan;
Raymond J. Michaels, Mundelein,
both of Ill.

[73] Assignee: Abbott Laboratories, North Chicago, Ill.

[21] Appl. No.: 963,666

[22] Filed: Nov. 24, 1978

[51] Int. Cl.$^2$ ............................ A01N 9/00; A01N 9/20
[52] U.S. Cl. ..................................... 424/330; 424/304
[58] Field of Search ................................ 424/364, 330

[56] References Cited

U.S. PATENT DOCUMENTS 2,961,372  11/1960  Eden ................................ 424/330

OTHER PUBLICATIONS

Patent Journal Including Trade Marks and Designs; vol. 8, No. 3 (1975) p. 156.

Derwent Farm DDC #65704V, Abst. of Netherlands Pat. 7402-704 (1261974).

Primary Examiner—Allen J. Robinson
Attorney, Agent, or Firm—Paul D. Burgauer; Robert L. Niblack

[57] ABSTRACT

It has been found that compounds of the structure

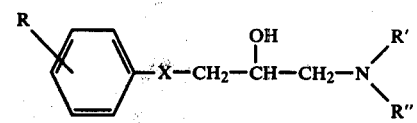

wherein X is O, S or $SO_2$, R represents H or one or more halogen, loweralkyl, —CH=CH—CH=CH—, CN, $NO_2$, loweralkyloxy, loweralkylcarbonyl or loweralkylmercapto, R' is H, loweralkyl, benzyl or R", and R" is $CH_2C\equiv CH$, $CMe_2C\equiv CH$ or $CHMeC\equiv CH$ are excellent insect ovicides.

10 Claims, No Drawings

OVICIDES

DETAILED DESCRIPTION OF THE INVENTION

Many compounds of the nature of 3-substituted amino-2-hydroxypropyl ethers have been known to be active as beta-adrenergic blockers. Some of these types of ethers also exhibit some insecticidal activity. It has been found that particular compounds of this series have unique ovicidal activity.

The present invention is directed to the process of preventing maturation of eggs of crop-damaging insects, consisting essentially in applying to the habitat of said eggs and ovicidal amount of a compound of the formula

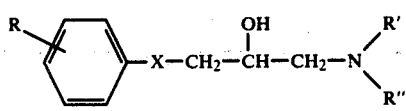 I wherein X is O, S or $SO_2$, R represents H or one or more halogen, loweralkyl, $-CH=CH-CH=CH-$, CN, $NO_2$, loweralkyloxy, loweralkylcarbonyl or loweralkylmercapto, R' is H, loweralkyl, benzyl or R", and R" is $CH_2C\equiv CH$, $CMe_2C\equiv CH$ or $CHMeC\equiv CH$, and simple salts thereof, together with an agriculturally acceptable diluent. The above reference to "loweralkyl" is meant to include those alkyl groups that contain 1-4 carbon atoms. The compounds used in the present invention are generally known from Dutch Patent No. 7402-704 which discloses some of the above compounds as useful in treating coronary disorders.

Among the agriculturally acceptable diluents, water is the most convenient one, although water is seldom used alone as detergents, wetting agents and the like are often necessary or desirable to provide a more homogeneous solution or dispersion of the active material. Solid diluents are often more suitable than liquids, as storing, shipping and packaging is easier than in liquid products.

The compounds of the current invention may be applied in the form of emulsifiable concentrates, powders, granules or dusts. An agronomically acceptable carrier for the purposes of this invention includes any substance which can be used to dissolve, disperse or diffuse the above novel compounds, without impairing the effectiveness of the active ingredient, and which is not deleterious to the soil or the plant in any chemical or physical manner. Particularly favored compositions are those wherein the active ingredient is present in a range from 1-20% by weight and the mixture of active compound and the diluent form a water-emulsifyable concentrate or it is a wettable powder. Solid diluents of this nature are well known in the agricultural formulation art. They include clay, diatomaceous earth, bentonite, etc.

In formulating the composition of this invention, other components may be included to aid in the adsorption or absorption of the active ingredients by the plant. Components such as wetting agents, solubilizers, emulsifiers, humiditants, surfactants and other adjuvants useful for this purpose may be incorporated in the formulations.

The above compounds are preferably compounded with inert diluents to a liquid or solid composition containing between 10,000 and 200,000 ppm, particularly compositions containing 25,000 to 50,000 ppm. Such stock mixes are easily packaged and stable and can be diluted by the consumer to the necessary concentrations of between 500 to 2,500 ppm.

In a general embodiment, the compounds used in the current invention are made by reacting epichlorohydrin with the appropriate alcohol, mercaptan or sulfinic acid ester of formula R-XH wherein R and X have the above meaning. This reaction is well known and many of the intermediate epoxypropyl ethers, mercaptans or sulfinic acids have been described previously; other analogs thereof are made in identical manner.

Subsequently, the above 1-substituted-2,3-propylene oxide is condensed with the appropriate amine of formula R'NHR" wherein R" represents the new, optionally methyl-substituent propargyl group. This reaction is best carried out at the reflux temperature of the reaction medium which is an inert liquid such as a fatty ahcohol, an ether or an aromatic hydrocarbon, preferably chosen to boil below about 120° C. The desired product is then removed by solvent evaporation and purified by crystallization.

In order to illustrate specific embodiments of the present invention, reference is made to the following examples which, however, are not intended to be limiting the scope of this invention.

EXAMPLE 1

A solution of 6.6 g. of 1-p-tolyloxy-2,3-epoxypropane and 2.2 g. of propargylamine in 25 ml. of ethanol is refluxed for six hours, followed by removal of the alcohol under reduced pressure. Upon standing, the residue crystallizes and upon recrystallization from cyclohexane, white crystals of 1-propargylamino-3-p-tolyloxy-2-propanol are obtained; m.p. 58°-60° C.

EXAMPLE 2

By refluxing excess propargylamine with 1-p-chlorophenlthio-2,3-epoxypropane in ethanol and following the procedure of Example 1, 1-propargylamino-3-p-chlorophenylthio-2-propanol is produced; m.p. 83°-86° C.

EXAMPLE 3

In the manner described in Example 1, condensation of 1.1 g. of propargylamine with 2.32 g. of p-chlorophenylsulfonyl-2,3-expoxypropane produces 1.7 g. of 1-propargylamino-3-p-chlorophenylsulfonyl-2-propanol; m.p. 91°-92° C.

EXAMPLE 4

Upon refluxing 6.36 g. of 1-p-chlorophenoxy-2,3-epoxypropanol with 5 g. of N-benzylpropargylamine in 50 ml. of ethanol and subsequent removal of the solvent as in Example 1, a yellow oil is obtained. Placing this oil on a silica gel column and eluting said column with ethyl acetate produces the pure yellow liquid 1-(N-benzylpropargylamino)-3-p-chlorophenoxy-2-propanol which shows IR and NMR spectra in accordance with its structure and proper analyses for $C_{19}H_{20}NO_2Cl$.

EXAMPLES 5-24

The compounds shown in Table I are all made by following the general directions shown in the preceding examples. They are listed by their structure in accordance with formula I (X=O) and their physical characteristics (and crystallization solvent). In all instances, the microanalyses are in good agreement with the calculated values for the particular compound named by structure. All temperatures are given in centigrade degress.

Table I

| Ex. # | R | R' | R" | °C.(Cryst. Solvent) |
|---|---|---|---|---|
| 5 | 4-Cl | H | propargyl | 75-7° (benzene) |
| 6 | H | H | propargyl | 74-5° (benzene) |
| 7 | 3-Cl | H | propargyl | 76-7° (cyclohexane) |
| 8 | 2-Cl | H | propargyl | 73-4° (benzene) |
| 9 | 3-Me | H | propargyl | 55-8° (cyclohexane) |
| 10 | 4-t-Bu | H | propargyl | 68-9° (cyclohexane) |
| 11 | 4-cyano | H | propargyl | 130-1° (MeCOEt) |
| 12 | 4-EtO | H | propargyl | 69-70° (cyclohexane) |
| 13 | 4-nitro | H | propargyl | 109-10° (MeOH) |
| 14 | 4-MeS | H | propargyl | 67-8° (benzene) |
| 15 | 4-MeCO | H | propargyl | 81-3° (MeCOOEt) |
| 16 | 3,4-Cl | H | propargyl | 104-5° (MeCOOEt) |
| 17 | 3,4-ME | H | propargyl | 65-6° (MeCOOEt) |
| 18 | 3-Me-4-MeS | H | propargyl | 67-8° (MeCOOEt) |
| 19 | 2,3,4,5,6-Cl | H | propargyl | 129-30° (benzene) |
| 20 | 2,3-(-CH=CH-)$_2$ | H | propargyl | 81-2° (benzene) |
| 21 | 4-Cl | Me | propargyl | oil |
| 22 | 4-Cl | R" | propargyl | oil |
| 23 | 4-Cl | H | dimethylpropargyl | 110-2° (ethanol) |
| 24 | 4-Cl | Me | methylpropargyl | oil |

The above compounds are evaluated as follows:

Fresh strips are taken from an appropriate cage of young adult cabbage loopers. This strip is disinfected for 10 minutes in a 10% formaldehyde solution. This step is necessary to surface sterilize the eggs to prevent extraneous mortality to newly emerged larvae from viruses and other pathogens. After treatment in the formaldehyde solution, egg strips are rinsed in running tap water for thirty minutes and then allowed to air dry. Following drying, the egg strips are cut into 1 inch squares. One square containing no less than 10 eggs is used for each test compound. Initial tests are carried out at 500 ppm made from a stock solution of 50,000 ppm in a DMF/isopropanol 1:3 (vol.) mixture containing 4% of a commercial wetting agent; the dilutent is a 70% aqueous acetone mixture.

An egg patch is placed into a Buchner funnel, attached to a vacuum source. Ten ml. aliquots of the appropriate compound are poured directly onto the patch. The chemical is immediately removed by suction. The egg patch is allowed to air dry and the number of eggs per patch is recorded. The treated eggs are then placed in a disposable petri dish (100×20 mm.) containing 30 ml. of normal looper rearing media (casein, alfalfa meal, wheat germ diet). A disc of filter paper 11 cm. in diameter is placed over the dish. The plastic lid is then pressed over the filter paper to seal the dish, which are then incubated at 30±1 degrees C. for six days.

To evaluate activity, the number of larvae emerging from each egg patch are counted. The resulting count is compared to the number of eggs contained in the patch and percent emergence is then calculated. Active compounds at 500 ppm are retested at 250 ppm.

The results are shown under heading A of Table II (A' corresponds with 250 ppm), using the following ratings: 0–20% emergence=3; 20–50% emergence=2; 50–75% emergence=1 and >75% emergence=0.

In the same fashion as above, some of the above compounds are also tested against eggs *Heliothis zea* (corn-ear worm) and *Heliothis verescens* (tobacco bud worm) at 500 ppm. The results are shown in columns B and C. In these tests, the larvae are counted after three days instead of the above 6-day span.

Table II

| Compound of Example No. | A | A' | B | C |
|---|---|---|---|---|
| 1 | 3 | 3 | 3 | 1 |
| 2 | 3 | 3 | 3 | 1 |
| 3 | 1 | NT | NT | NT |
| 4 | 3 | 2 | NT | NT |
| 5 | 3 | 3 | 2 | 2 |
| 7 | 3 | 3 | 2 | 1 |
| 9 | 3 | 3 | 2 | 1 |
| 16 | 3 | 3 | 2 | 1 |
| 19 | 1 | 1 | 3 | 1 |
| 20 | 2 | 1 | NT | NT |

NT = not tested

As seen from the above results, the compounds used for the current procedure are highly effective in preventing larvae development. This ovicidal activity is of great commercial interest because of the damage that can be caused by the hatching insects. While the above tests are directed to specific eggs only, it will be understood that these compounds have ovicidal effect over a much wider variety of insect eggs; however, the above identified species are among the most difficult ones to combat and it is generally accepted that ovicides used successfully against cabbage loopers or corn-ear worms are effective also in combating the hatching of eggs of other crop-damaging insects, i.e., the entire heliothis family.

As described above, the current compounds are commonly applied in diluents, preferably at a concentration of 250-2500 ppm. Wettable powders which may optionally contain other ingredients useful in combating agricultural pests (fungicides, insecticides, etc.) are ordinarily prepared by use of 0.01–0.1% by weight of a wetting agent such as an alkyl sulfate, an aralkyl sulfonate, a sulfosuccinate, a polyethylene glycol ether or the like. Dusting powders are made with the current ovicides and a finely divided, inert diluent. In this instance, the above range of 0.025–0.25% by weight of the new ovicide is also preferred and again, other agricultural control agents may be included in such a compound.

The above examples are directed to the use of many of the compounds of the depicted structure. Their simple salts can be used in similar fashion and frequently, their preparation is easier than that of the free compound as it allows the use of the appropriate acid in the isolation or purification steps. Among the most common acids that frequently add to the above bases are the hydrochloric, sulfuric, acetic, oxalic, maleic or succinic acids. Other organic acids can also be used but they are less economical than the above.

I claim:

1. A method of combating the hatching of eggs of crop-damaging insects consisting essentially in applying to the habitat of said eggs an ovicidal amount of a compound of the formula

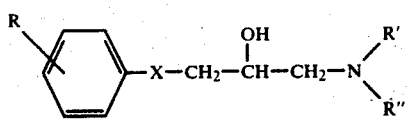

wherein X is O, S or SO₂, R represents H or one or more halogen, loweralkyl, —CH═CH—CH═CH— attached to two adjacent positions, CN, NO₂, loweralkyloxy, loweralkylcarbonyl or loweralkylmercapto, R' is H, loweralkyl, benzyl or R", and R" is CH₂C≡CH, CMe₂C≡CH or CHMeC≡CH and simple acid addition salts thereof, together with an agriculturally acceptable carrier.

2. The method of claim 1 wherein said ovicidal compound is present in said carrier at a concentration of 0.025-0.25% by weight.

3. The method of claim 2 wherein R is chlorine, X is oxygen, R' is hydrogen and R" is propargyl.

4. The method of claim 3 wherein said chlorine is in the 4-position.

5. The method of claim 2 wherein R=p-Cl X is O, R' is benzyl and R" is propargyl.

6. The method of claim 2 wherein R=p-methyl, X=O, R' is H and R" is propargyl.

7. The method of claim 2 wherein R=p-Cl, X=S, R' is H and R" is propargyl.

8. The method of claim 2 wherein R=m-Cl, X=O, R' is H and R" is propargyl.

9. The method of claim 2 wherein R=m-methyl, X=O, R' is H and R" is propargyl.

10. The method of claim 2 wherein R=3,4-dichloro, X=O, R' is H and R" is propargyl.